United States Patent
Matsuo et al.

(10) Patent No.: US 11,567,025 B2
(45) Date of Patent: Jan. 31, 2023

(54) GAS SENSOR

(71) Applicant: TDK Corporation, Tokyo (JP)

(72) Inventors: Yutaka Matsuo, Tokyo (JP); Yoshio Kaita, Tokyo (JP)

(73) Assignee: TDK CORPORATION, Tokyo (JP)

( * ) Notice: Subject to any disclaimer, the term of this patent is extended or adjusted under 35 U.S.C. 154(b) by 5 days.

(21) Appl. No.: 17/265,958

(22) PCT Filed: Jun. 20, 2019

(86) PCT No.: PCT/JP2019/024432
§ 371 (c)(1),
(2) Date: Feb. 4, 2021

(87) PCT Pub. No.: WO2020/031517
PCT Pub. Date: Feb. 13, 2020

(65) Prior Publication Data
US 2021/0293735 A1 Sep. 23, 2021

(30) Foreign Application Priority Data
Aug. 10, 2018 (JP) .............................. JP2018-151364

(51) Int. Cl.
*G01N 27/18* (2006.01)
(52) U.S. Cl.
CPC .................................. *G01N 27/18* (2013.01)
(58) Field of Classification Search
CPC .............................. G01N 27/18; G01N 33/004
See application file for complete search history.

(56) References Cited

U.S. PATENT DOCUMENTS

| 5,048,336 A * | 9/1991 | Sugihara | G01N 27/18 338/35 |
| 5,297,419 A * | 3/1994 | Richardson | G01N 27/18 422/90 |
| 5,551,283 A * | 9/1996 | Manaka | G01F 1/69 73/75 |
| 6,019,505 A * | 2/2000 | Bonne | G01N 27/18 73/204.17 |
| 6,361,204 B1 * | 3/2002 | Marzoli | G01N 27/18 374/10 |

(Continued)

FOREIGN PATENT DOCUMENTS

| JP | 2016-050825 A | 4/2016 |
| JP | 20-17-156293 A | 9/2017 |

OTHER PUBLICATIONS

Machine translation of JP6679993 (equivalent of JP 2017156293) (Year: 2017).*

(Continued)

*Primary Examiner* — David J Bolduc
(74) *Attorney, Agent, or Firm* — McDermott Will & Emery LLP (57) ABSTRACT

A gas sensor includes a first thermistor as a detection element, a second thermistor as a reference element, a first heater for heating the first thermistor, a second heater for heating the second thermistor, and a control circuit that heats the first and second heaters such that the second thermistor has a higher temperature than the first thermistor in a first period of time and that the first thermistor has a higher temperature than the second thermistor in a second period of time.

13 Claims, 9 Drawing Sheets

(56) References Cited

U.S. PATENT DOCUMENTS

| | | | | |
|---|---|---|---|---|
| 6,474,138 | B1* | 11/2002 | Chang | G01N 33/004 73/23.31 |
| 7,631,537 | B2* | 12/2009 | Tada | G01N 33/005 73/23.31 |
| 2002/0092780 | A1* | 7/2002 | Nadanami | G01N 27/4074 205/782 |
| 2005/0028580 | A1* | 2/2005 | Bauer | G01N 27/18 73/25.03 |
| 2007/0045129 | A1* | 3/2007 | Gu | G01N 25/4846 205/785 |
| 2009/0215180 | A1* | 8/2009 | Bos | G01N 27/122 422/82.12 |
| 2012/0029835 | A1* | 2/2012 | Xia | G01N 21/0303 385/12 |
| 2012/0247184 | A1* | 10/2012 | Kitanoya | G01N 27/18 73/25.05 |
| 2014/0020448 | A1* | 1/2014 | Matsukura | G01N 27/18 73/25.01 |
| 2015/0177184 | A1* | 6/2015 | Brezeanu | G01N 33/004 257/77 |
| 2016/0334376 | A1* | 11/2016 | Gellert | G01N 27/18 |
| 2018/0067067 | A1* | 3/2018 | Kale | G01N 27/18 |
| 2018/0292338 | A1* | 10/2018 | Liu | G01N 27/04 |
| 2018/0328872 | A1* | 11/2018 | Nakano | G01N 27/18 |
| 2019/0128827 | A1* | 5/2019 | Bao | G01N 25/482 |
| 2019/0204251 | A1* | 7/2019 | Nakano | H01L 27/04 |
| 2019/0204283 | A1* | 7/2019 | Lemkin | G01N 33/0098 |
| 2019/0353607 | A1* | 11/2019 | Kaita | G01N 27/028 |
| 2020/0080951 | A1* | 3/2020 | Nakano | G01N 27/18 |
| 2020/0348252 | A1* | 11/2020 | Mueller | G01N 33/0027 |
| 2021/0199612 | A1* | 7/2021 | Prajapati | G01N 27/18 |

OTHER PUBLICATIONS

Extended European Search Report issued in corresponding European Patent Application No. 19847665.7-1020, dated Mar. 18, 2022.
International Search Report issued in corresponding International Patent Application No. PCT/JP2019/024432, dated Aug. 20, 2019, with English translation.

* cited by examiner

GAS SENSOR

CROSS REFERENCE

This application is the U.S. National Phase under 35 US.C. § 371 of International Application No. PCT/JP2019/024432, filed on Jun. 20, 2019, which claims the benefit of Japanese Application No. 2018-151364, filed on Aug. 10, 2018, the entire contents of each are hereby incorporated by reference.

TECHNICAL FIELD

The present invention relates to a gas sensor for detecting gas contained in the atmosphere and, more particularly, to a gas sensor configured to connect a detection element and a reference element in series.

BACKGROUND ART

Gas sensors detect the concentration of a measurement target gas contained in the atmosphere. To improve detection accuracy, such gas sensor may be configured to connect a detection element and a reference element in series and acquire an output signal from the connection point therebetween. For example, a gas sensor described in Patent Document 1 is configured to connect the detection element and reference element in series and heat them to their respective predetermined temperatures at detection timing.

Further, the gas sensor described in Patent Document 1 heats the reference element to a high temperature at non-detection timing to reduce the difference in thermal history between the detection element and the reference element.

CITATION LIST

Patent Document

[Patent Document 1] JP 2017-156293A

SUMMARY OF THE INVENTION

Problem to be Solved by the Invention

However, the gas sensor described in Patent Document 1 selectively heats only the reference element at non-detection timing, generating a difference in the number of times of heating between the detection element and the reference element. This makes it difficult to set the heating temperature and heating time of the reference element at non-detection timing and, thus, it is not easy to sufficiently reduce the difference in thermal history between the detection element and the reference element.

It is therefore an object of the present invention to provide a gas sensor capable of reducing the difference in temperature load between the detection element and the reference element easily and more accurately.

Means for Solving the Problem

A gas sensor according to the present invention includes: a detection element whose resistance value changes in accordance with the concentration of a gas to be detected; a reference element connected in series to the detection element; a first heater for heating the detection element; a second heater for heating the reference element; and a control circuit that heats the first and second heaters such that the reference element has a higher temperature than the detection element in a first period of time and that the detection element has a higher temperature than the reference element in a second period of time.

According to the present invention, the reference element has a higher temperature load than the detection element in the first period of time, and the detection element has a higher temperature load than the reference element in the second period of time, so that repeating the first and second periods of time can easily reduce the difference in thermal history between the detection element and the reference element.

In the present invention, the control circuit may calculate the concentration of the gas to be detected based on a potential appearing at a connection point between the detection element and the reference element in one of the first and second periods of time. Thus, it is possible to calculate the concentration of the gas to be detected in one of the first and second periods of time.

In the present invention, the control circuit may heat the first and second heaters such that the detection element and the reference element have a first temperature and a second temperature, respectively, in the first period of time and that the reference element and the detection element have the first temperature and the second temperature, respectively, in the second period of time. This allows the thermal histories of the detection element and reference element to substantially coincide with each other.

In the present invention, the lengths of the first and second periods of time may be equal to each other. This allows the thermal histories of the detection element and reference element to coincide with each other more accurately.

In the present invention, the gas to be detected may be $CO_2$ gas, the heating temperature of the detection element in the first period of time may be in the range of 100° C. to 200°, and the heating temperature of the reference element in the first period of time may be in the range of 250° C. to 350° C. This allows the concentration of $CO_2$ gas to be detected with high sensitivity.

In the present invention, the detection element and reference element may each have a MEMS structure, and the length of the first period of time may be in the range of 50 ms to 400 ms. This can minimize power consumption.

In the present invention, the ratio of the resistance value of the detection element and the resistance value of the reference element may be in the range of 0.5 to 2.0. This allows the concentration of $CO_2$ gas to be detected with high sensitivity.

In the present invention, the detection element and reference element may be formed on mutually different chips. This makes the heat of the heater provided on one chip less likely to be conducted to the other chip to prevent the detection element and reference element from being suffered from thermal interference from the heaters therefor, thereby suppressing a reduction in sensitivity. Further, the difference in thermal history can be further reduced.

Advantageous Effects of the Invention

As described above, according to the present invention, the thermal histories of the detection element and reference element can be easily reduced. This can suppress the temporal change of the gas sensor.

MODE FOR CARRYING OUT THE INVENTION

Preferred embodiments of the present invention will be explained below in detail with reference to the accompanying drawings.

Figure 1:
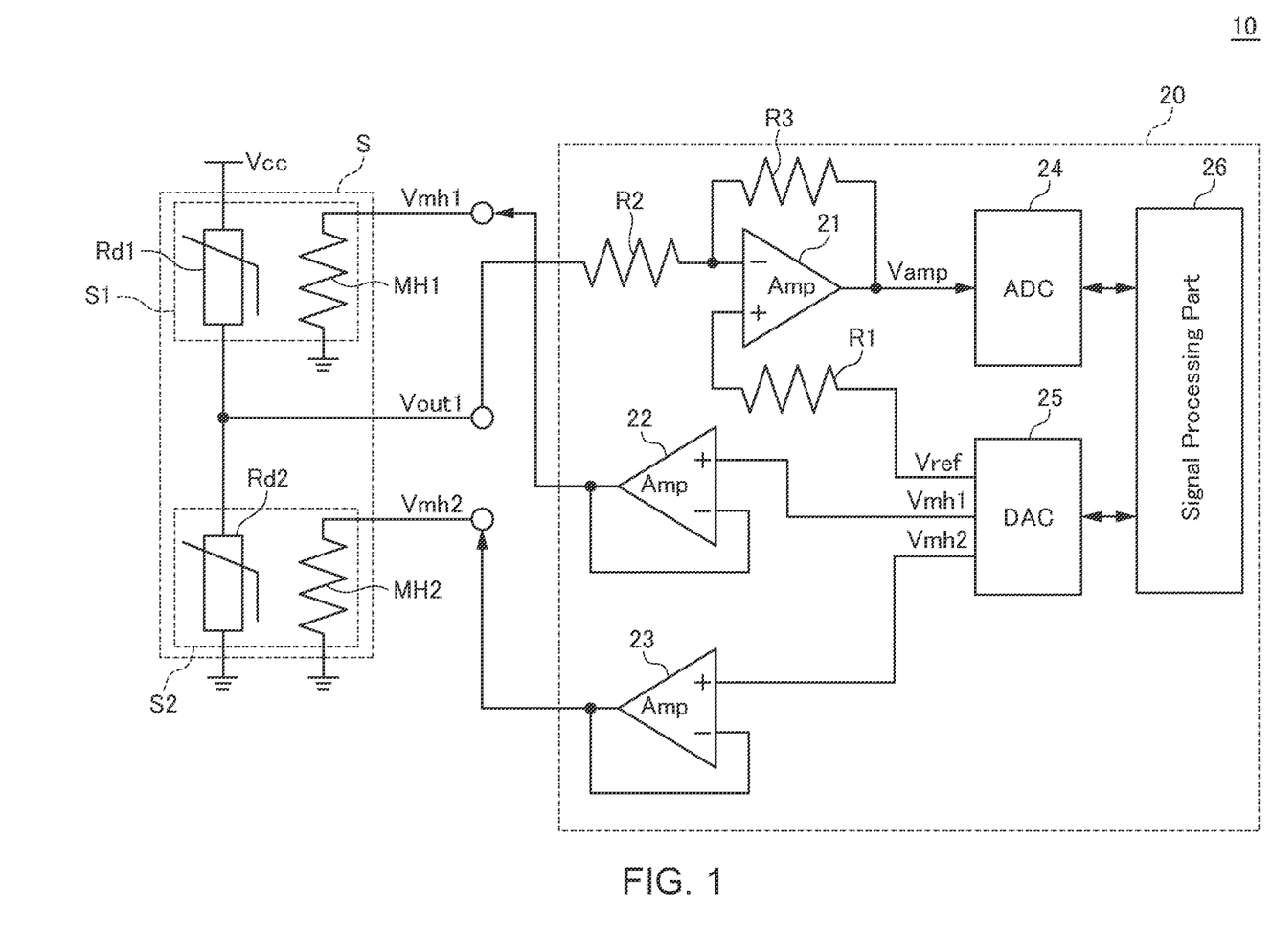
FIG. 1 is a circuit diagram illustrating the configuration of a gas sensor 10 according to a preferred embodiment of the present invention.

FIG. 1 is a circuit diagram illustrating the configuration of a gas sensor 10 according to a preferred embodiment of the present invention.

As illustrated in FIG. 1, the gas sensor 10 according to the present embodiment includes a sensor part S and a control circuit 20. Although not particularly limited, the gas sensor according to the present embodiment detects the concentration of $CO_2$ gas in the atmosphere.

The sensor part S is a heat conduction type gas sensor for detecting the concentration of $CO_2$ gas to be detected and has a first sensor part S1 and a second sensor part S2. The first sensor part S1 includes a first thermistor Rd1 serving as a detection element and a first heater resistor MH1 that heats the first thermistor Rd1. Similarly, the second sensor part S2 includes a second thermistor Rd2 serving as a reference element and a second heater resistor MH2 that heats the second thermistor Rd2. As illustrated in FIG. 1, the first and second thermistors Rd1 and Rd2 are connected in series between a wiring supplied with a power supply potential Vcc and a wiring supplied with a ground potential GND. The first and second thermistors Rd1 and Rd2 are each made of a material having a negative resistance temperature coefficient, such as a composite metal oxide, amorphous silicon, polysilicon, or germanium.

The first thermistor Rd1 is heated by the first heater resistor MH1. The heating temperature of the first thermistor Rd1 by the first heater resistor MH1 is, e.g., 150° C. at detection timing. When $CO_2$ gas is present in the measurement atmosphere in a state where the first thermistor Rd1 is heated to 150° C., heat dissipation characteristics of the first thermistor Rd1 changes according to the $CO_2$ gas concentration. This change appears as a change in the resistance value of the first thermistor Rd1.

The second thermistor Rd2 is heated by the second heater resistor MH2. The heating temperature of the second thermistor Rd2 by the second heater resistor MH2 is, e.g., 300° C. at detection timing. Even when $CO_2$ gas is present in the measurement atmosphere in a state where the second thermistor Rd2 is heated to 300° C., the resistance value of the second thermistor Rd2 hardly changes.

The ratio of the resistance value of the first thermistor Rd1 and that of the second thermistor Rd2 at a room temperature (25° C.) is about 10. For example, the resistance values of the first and second thermistors Rd1 and Rd2 at a room temperature are 280 k$\Omega$ and 2800 k$\Omega$, respectively. When the first and second thermistors Rd1 and Rd2 are heated, their resistance values are reduced. As described above, the heating temperature (e.g., 300° C.) of the second thermistor Rd2 at detection timing is higher than the heating temperature (e.g., 150° C.) of the first thermistor Rd1 at detection timing, so that, at detection timing, the ratio of the resistance value of the first thermistor Rd1 and the resistance value of the second thermistor Rd2 is in the range of 0.5 to 2.0, preferably, substantially 1. For example, the resistance value of the first thermistor Rd1 heated to 150° C. is 10 k$\Omega$, and the resistance value of the second thermistor Rd2 heated to 300° C. is also 10 k$\Omega$.

The first and second thermistors Rd1 and Rd2 are connected in series as described above, and a detection signal Vout1 is output from the connection point therebetween. The output detection signal Vout1 is input to the control circuit 20. The amount of change in the detection signal Vout1 based on the $CO_2$ gas concentration becomes larger as the resistance values of the first and second thermistors Rd1 and Rd2 at detection timing are closer, and detection sensitivity is improved. In this respect, the ratio of the resistance values of the first and second thermistors Rd1 and Rd2 at detection timing is preferably in the range of 0.5 to 2.0, and particularly preferably, substantially 1.

The control circuit 20 has differential amplifiers 21 to 23, an AD converter (ADC) 24, a DA converter (DAC) 25, a signal processing part 26, and resistors R1 to R3. The differential amplifier 21 compares the detection signal Vout1 and a reference voltage Vref and amplifiers the detected difference. The gain of the differential amplifier 21 is adjusted to any value by the resistors R1 to R3. An amplified signal Vamp output from the differential amplifier 21 is input to the AD converter 24.

The AD converter 24 converts the amplified signal Vamp into a digital signal and supplies the obtained value to the signal processing part 26. On the other hand, the DA converter converts a reference signal supplied from the signal processing part 26 to an analog signal to generate the reference voltage Vref and generates control voltages Vmh1 and Vmh2 to be supplied respectively to the first and second heater resistors MH1 and MH2. The control voltage Vmh1 is applied to the first heater resistor MH1 through a differential amplifier 22 which is a voltage follower. Similarly, the control voltage Vmh2 is applied to the second heater resistor MH2 through a differential amplifier 23 which is a voltage follower.

Figure 2:
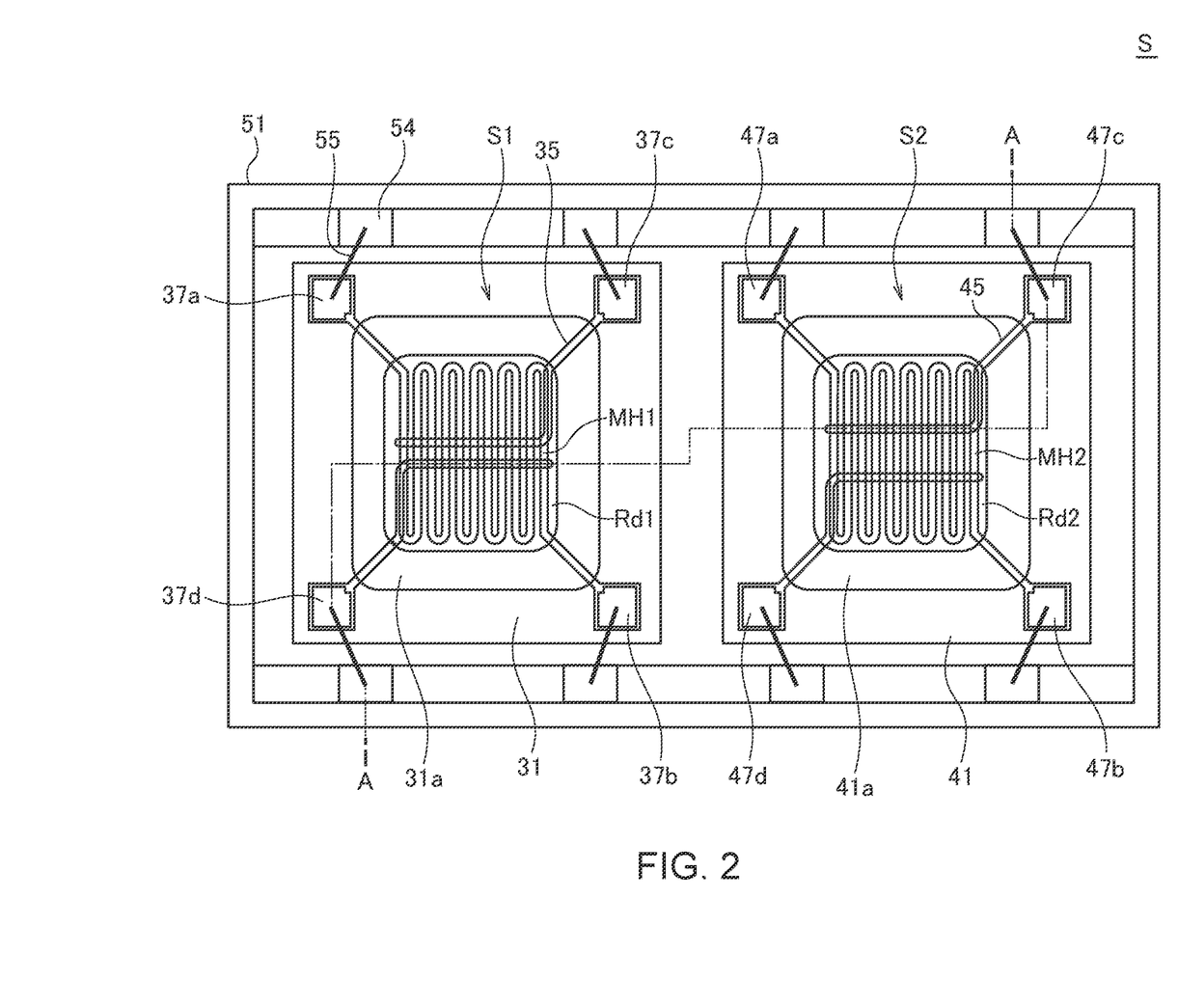
FIG. 2 is a top view for explaining the configuration of the sensor part S.
Figure 3:
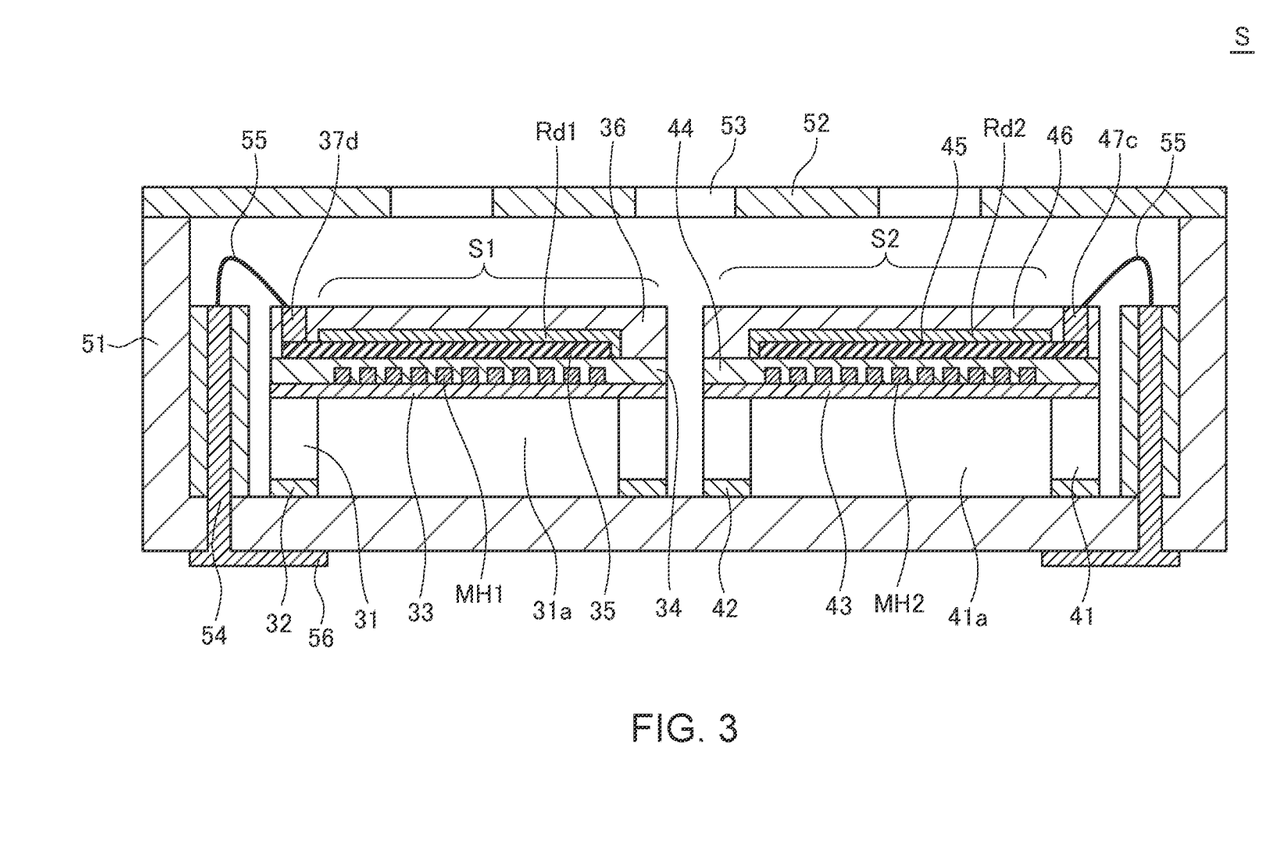
FIG. 3 is a cross-sectional view taken along line A-A in FIG. 2.

FIG. 2 is a top view for explaining the configuration of the sensor part S. FIG. 3 is a cross-sectional view taken along line A-A in FIG. 2. The drawings are schematic, and for explanatory convenience, the relation between thickness and plane dimension, ratio between the thicknesses of devices, and the like may be different from those in the actual structure within a range in which the effect of the present embodiment can be obtained.

The sensor part S is a heat conduction type gas sensor that detects the concentration of a gas based on a change in heat dissipation characteristics according to the $CO_2$ gas concentration and has, as illustrated in FIGS. 2 and 3, two sensor parts S1 and S2 and a ceramic package 51 housing the sensor parts S1 and S2.

The ceramic package 51 is a box-shaped case having an opened upper part, and a lid 52 is provided at the upper part.

The lid 52 has a plurality of vent holes 53, through which $CO_2$ gas in the atmosphere can flow into the ceramic package 51. In FIG. 2, the lid 52 is omitted for ease of viewing.

The first sensor part S1 includes insulating films 32 and 33 formed respectively on the lower and upper surfaces of a substrate 31, a first heater resistor MH1 provided on the insulating film 33, a heater protective film 34 covering the first heater resistor MH1, a first thermistor Rd1 and a thermistor electrode 35 which are provided on the heater protective film 34, a thermistor protective film 36 covering the first thermistor Rd1 and thermistor electrode 35.

There is no particular restriction on the material of the substrate 31 as long as it has an adequate mechanical strength and is suitable for fine processing such as etching, and, examples thereof include a silicon single crystal substrate, a sapphire single crystal substrate, a ceramic substrate, a quartz substrate, a glass substrate, and the like. A cavity 31a is provided at a position overlapping the first heater resistor MH1 in a plan view so as to suppress conduction of heat due to the first heater resistor MH1 to the substrate 31. A part where the substrate 31 is removed by the cavity 31a is called a membrane. The presence of the membrane reduces heat capacity by the thinning of the substrate 31, allowing heating to be achieved with less power consumption.

The insulating films 32 and 33 are each made of an insulating material such as silicon oxide or silicon nitride. When silicon oxide is used as the insulating films 32 and 33, a film deposition method such as a thermal oxidation method or a CVD (Chemical Vapor Deposition) method may be used. There is no particular restriction on the thickness of the insulating films 32 and 33 as long as the insulating property thereof is ensured and may be, e.g., about 0.1 μm to 1.0 μm. Particularly, the insulating film 33 is used also as an etching stop layer when the cavity 31a is formed in the substrate 31, so that the thickness thereof is preferably set to a value suitable for fulfilling the function as the etching stop layer.

The first heater resistor MH1 is made of a conductive substance whose resistivity changes depending on temperature and is preferably made of a metal material having a comparatively high melting point, such as molybdenum (Mo), platinum (Pt), gold (Au), tungsten (W), tantalum (Ta), palladium (Pd), iridium (Ir), or an alloy containing two or more of them. Among them, a conductive material that can be subjected to high accuracy dry etching such as ion milling is preferable, and more preferably, it contains platinum (Pt) having high corrosion resistance as a main component. Further, an adhesion layer such as a titanium (Ti) layer is preferably formed as a base of Pt so as to improve adhesion with respect to the insulating film 33.

The heater protective film 34 is formed above the first heater resistor MH1. The heater protective film 34 is preferably made of the same material as the insulating film 33. The first heater resistor MH1 generates violent thermal changes (repetition of temperature rises between room temperature to 150° C. or 300° C., for example, and then a drop to room temperature again), so that strong thermal stress is applied to the insulating film 33 and heater protective film 34. When being continuously subject to the thermal stress, the insulating film 33 and heater protective film 34 may suffer damage such as interlayer peeling or crack. However, when the insulating film 33 and the heater protective film 34 are made of the same material, material characteristics thereof are the same, and adhesion strength therebetween is high, so that the damage such as interlayer peeling or crack is less likely to occur as compared to when the insulating film 33 and the heater protective film 34 are made of mutually different materials. When silicon oxide is used as the material of the heater protective film 34, film deposition may be performed by a thermal oxidation method or a CVD method. The film thickness of the heater protective film 34 is not particularly restricted as long as insulation between the first thermistor Rd1 and the thermistor electrode 35 can be ensured and may be, e.g., 0.1 μm to 3.0 μm.

The first thermistor Rd1 is made of a material having a negative resistance-temperature coefficient, such as a composite metal oxide, amorphous silicon, polysilicon, or germanium and can be formed by using a thin-film process such as a sputtering method or a CVD method. The film thickness of the first thermistor Rd1 may be adjusted according to a target resistance value. The reason that the thermistor is used as a temperature-sensitive resistive element is that the thermistor is larger in resistance temperature coefficient than a platinum temperature detector and can thus obtain high detection sensitivity. Further, heat generation of the first heater resistor MH1 can efficiently be detected because of the thin-film structure.

The thermistor electrode 35 is configured of a pair of electrodes arranged spaced apart from each other at a predetermined interval, and the first thermistor Rd1 is provided between the pair of thermistor electrodes 35. With this configuration, the resistance value between the pair of thermistor electrodes 35 is determined by the resistance value of the first thermistor Rd1. The thermistor electrode 35 may be made of a conductive substance that can endure a process such as a film deposition step and a heat treatment process for the first thermistor Rd1 and is preferably made of a material having a comparatively high melting point, such as molybdenum (Mo), platinum (Pt), gold (Au), tungsten (W), tantalum (Ta), palladium (Pd), iridium (Ir), or an alloy containing two or more of them.

The first thermistor Rd1 and thermistor electrode 35 are covered with the thermistor protective film 36. When the first thermistor Rd1 is brought into contact with a material having reducibility so as to make it turn into a high-temperature state, the material deprives the thermistor of oxygen to cause a reduction, thus affecting thermistor characteristics. To prevent this, an insulating oxide film having no reducibility, such as silicon oxide film, is preferably used as the material of the thermistor protective film 36.

As illustrated in FIG. 2, both ends of the first heater resistor MH1 are connected respectively to electrode pads 37a and 37b provided on the surface of the thermistor protective film 36. Further, both ends of the thermistor electrode 35 are connected respectively to electrode pads 37c and 37d provided on the surface of the thermistor protective film 36. The electrode pads 37a to 37d are connected to a package electrode 54 installed to the ceramic package 51 through a bonding wire 55. The package electrode 54 is connected to the control circuit 20 illustrated in FIG. 1 through an external terminal 56 provided on the back surface of the ceramic package 51.

As described above, the first sensor part S1 has a configuration in which the first heater resistor MH1 and first thermistor Rd1 are laminated on the substrate 31, so that heat generated by the first heater resistor MH1 is efficiently conducted to the first thermistor Rd1.

Similarly, the second sensor S2 includes insulating films 42 and 43 formed respectively on the lower and upper surfaces of a substrate 41, a second heater resistor MH2 provided on the insulating film 43, a heater protective film 44 covering the second heater resistor MH2, a second thermistor Rd2 and a thermistor electrode 45 which are provided on the heater protective film 44, and a thermistor protective film 46 covering the second thermistor Rd2 and thermistor electrode 45.

The substrate 41 is made of the same material as the substrate 31 used for the first sensor part S1 and has the same configuration as the substrate 31. That is, a cavity 41a is provided at a position overlapping the second heater resistor MH2 in a plan view so as to suppress heat due to the second heater resistor MH2 from conducting to the substrate 41. The insulating films 42 and 43 are made of the same material (insulating material such as silicon oxide or silicon nitride) as the insulating films 32 and 33. The insulating films 42 and 43 have the same thickness as the insulating films 32 and 33.

The second heater resistor MH2, heater protective film 44, second thermistor Rd2, thermistor electrode 45, and thermistor protective film 46 have the same configurations as the first heater resistor MH1, the heater protective film 34, the first thermistor Rd1, the thermistor electrode 35, and the thermistor protective film 36, respectively, used for the first sensor part S1. Both ends of the second heater resistor MH2 are connected respectively to electrode pads 47a and 47b provided on the surface of the thermistor protective film 46. Further, the both ends of the thermistor electrode 45 are connected respectively to electrode pads 47c and 47d provided on the surface of the thermistor protective film 46. The electrode pads 47a to 47d are connected to the package electrode 54 fitted in the ceramic package 51 through the bonding wire 55.

The thus configured first and second sensor parts S1 and S2 are each produced in multiple numbers in a wafer state at a time, followed by dicing into individual pieces, and then fixed to the ceramic package 51 using a die paste (not illustrated). Thereafter, electrode pads 37a to 37d and 47a to 47d are connected to their corresponding package electrodes 54 through the bonding wires 55 using a wire bonding machine. As the material of the bonding wire 55, a metal having low resistance, such as Au, Al, or Cu is preferably used.

Finally, adhesive resin (not illustrated) or the like is used to fix the lid 52 having the outside air vent holes 53 to the ceramic package 51. Although a substance contained in the adhesive resin is turned into gas during heating/curing of the adhesive resin (not shown), the gas is easily discharged outside the package through the vent holes 53, so that the first and second sensor parts S1 and S2 are hardly affected.

The thus accomplished the sensor part S is connected to the control circuit 20 or a power supply through the external terminal 56.

The configuration of the gas sensor 10 according to the present embodiment has thus been described above. As described above, in the gas sensor 10 according to the present embodiment, the first thermistor Rd1 serving as a detection element and the second thermistor Rd2 serving as a reference element are formed on mutually different chips, thus making the heat of the heater resistor provided on one chip less likely to be conducted to the other chip. This prevents the first and second thermistors Rd1 and Rd2 from being suffered from thermal interference from the heaters therefor, thereby suppressing a reduction in sensitivity. Further, the difference in thermal history is further reduced, resulting in a further improvement in detection accuracy.

The following describes the operation of the gas sensor 10 according to the present embodiment.

The gas sensor 10 according to the present embodiment utilizes a fact that the thermal conductivity of $CO_2$ gas significantly differs from the thermal conductivity of air to take out a change in the heat dissipation characteristics of the first and second thermistors Rd1 and Rd2 according to the $CO_2$ gas concentration as the detection signal Vout1.

Figure 4:
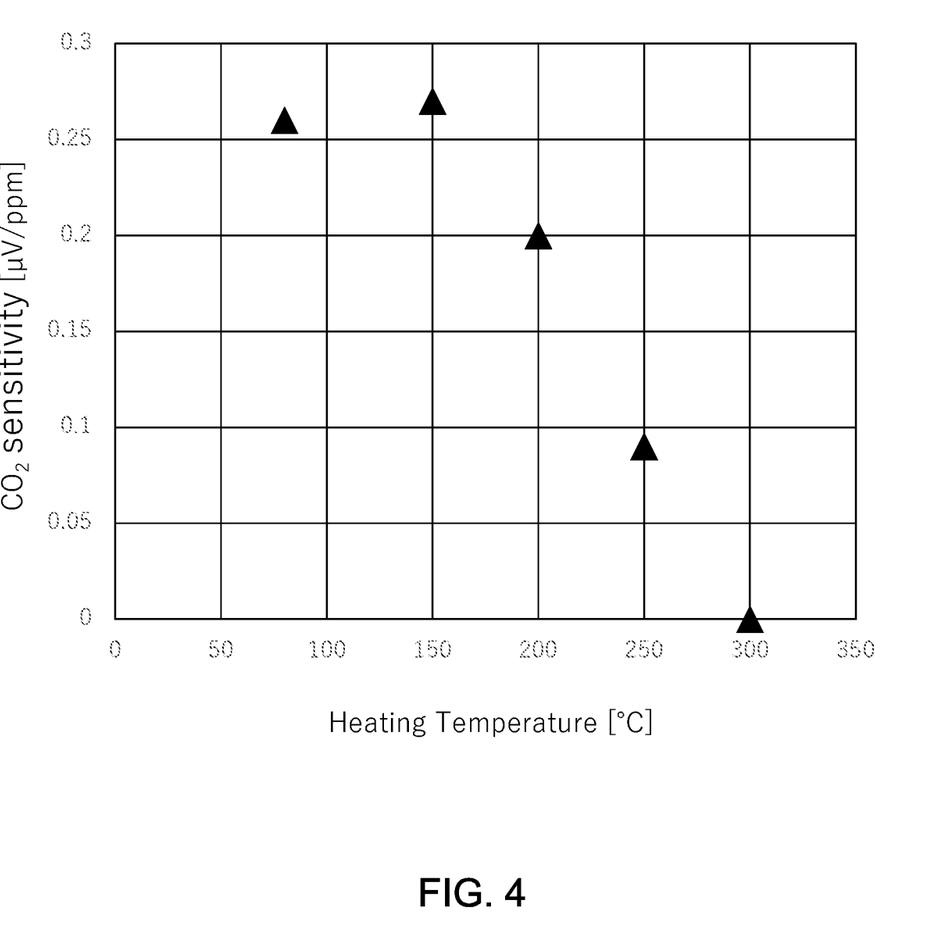
FIG. 4 is a graph illustrating the relationship between the heating temperature of the thermistors Rd1 and Rd2 and $CO_2$ sensitivity.

FIG. 4 is a graph illustrating the relationship between the heating temperature of the thermistors Rd1 and Rd2 and CO2 sensitivity.

As illustrated in FIG. 4, when the heating temperature of the thermistors Rd1 and Rd2 is in the range of 100° C. to 200° C., a sufficient sensitivity to the $CO_2$ gas concentration can be obtained, while when the heating temperature thereof is in the range of 250° C. to 300° C., the sensitivity to the $CO_2$ gas concentration decreases. In particular, when the heating temperature reaches 300° C., the sensitivity to the $CO_2$ gas concentration becomes substantially 0. Actually, a slight sensitivity to the $CO_2$ gas concentration exists even at a heating temperature of 300° C., but is significantly lower than the sensitivity at a heating temperature of 150° C. (about 1/10 or less) and can be substantially ignored.

Considering the above, at detection timing, the gas sensor 10 according to the present embodiment heats the first thermistor Rd1 to e.g., 150° C. to sufficiently increase the sensitivity to the $CO_2$ gas concentration and heats the second thermistor Rd2 to, e.g., 300° C. to substantially zero the sensitivity to the $CO_2$ gas concentration. Since the first and second thermistors Rd1 and Rd2 are connected in series, the level of the detection signal Vout1 indicates the $CO_2$ gas concentration.

Figure 5:
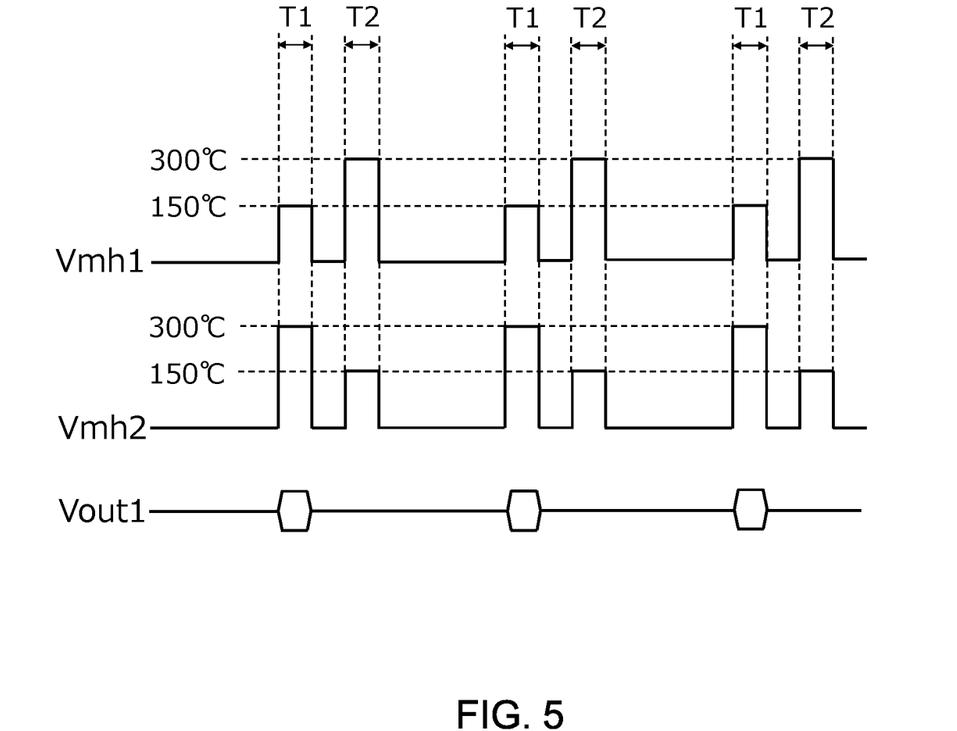
FIG. 5 is a timing chart illustrating the waveforms of the control voltages Vmh1 and Vmh2.

FIG. 5 is a timing chart illustrating the waveforms of the control voltages Vmh1 and Vmh2.

As illustrated in FIG. 5, in the present embodiment, a first period of time T1 in which the control voltage Vmh1 and control voltage Vmh2 reach their respective predetermined levels at the same time and a second period of time T2 in which the control voltage Vmh1 and control voltage Vmh2 reach their respective predetermined levels at the same time are alternately repeated. In the first period of time T1, the control voltage Vmh2 is set higher than the control voltage Vmh1, with the result that the heating temperature of the first thermistor Rd1 by the first heater resistor MH1 becomes, e.g., 150° C., and the heating temperature of the second thermistor Rd2 by the second heater resistor MH2 becomes, e.g., 300° C. In the first period of time T1, the detection signal Vout1 is sampled by the control circuit 20, and the $CO_2$ gas concentration is determined based on the sampled signal. The sampling period of the Vout1 is, e.g., 30 sec.

In the second period of time T2, the control voltage Vmh1 is set higher than the control voltage Vmh2, with the result that the heating temperature of the first thermistor Rd1 by the first heater resistor MH1 becomes, e.g., 300° C., and the heating temperature of the second thermistor Rd2 by the second heater resistor MH2 becomes, e.g., 150° C. In the second period of time T2, the control circuit 20 does not perform sampling of the detection signal Vout1.

Thus, in the second period of time T2, sampling of the detection signal Vout1 is not performed; however, a completely reverse temperature load to that in the first period of time T1 is applied to the first and second thermistors Rd1 and Rd2 to make the thermal histories of the first and second thermistors Rd1 and Rd2 coincide with each other. This makes it possible to easily and effectively suppress the temporal change of the gas sensor 10.

Figure 6:
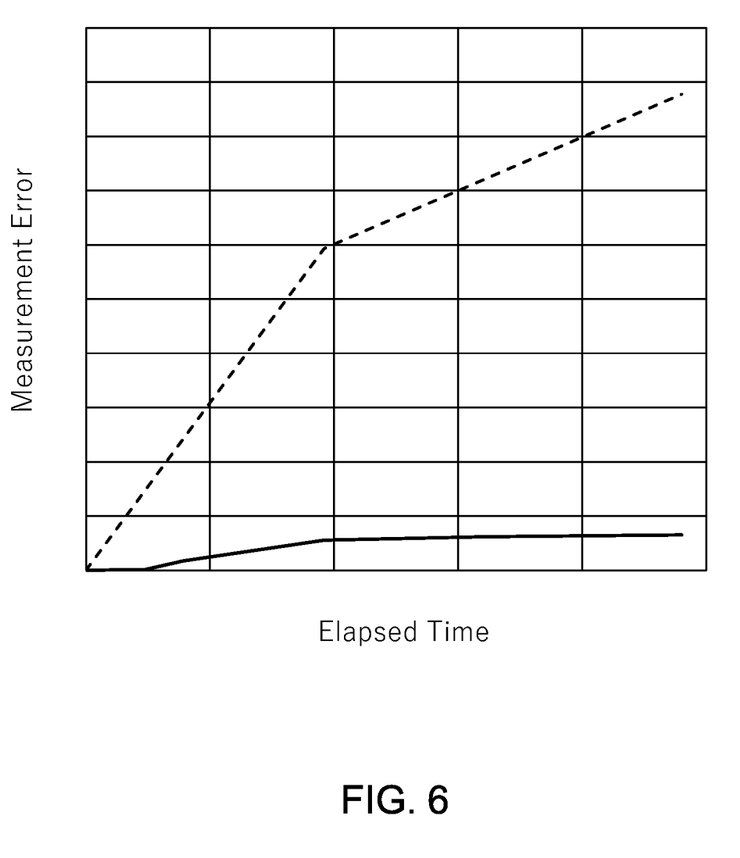
FIG. 6 is a graph for explaining the effect of the gas sensor 10.

FIG. 6 is a graph for explaining the effect of the present embodiment. The solid line denotes the temporal change of the gas sensor 10 according to the present embodiment, and the dashed line denotes the temporal change of the gas sensor 10 in a case where the heating operation in the second period of time T2 is omitted. As can be seen from FIG. 6, the temporal change of the gas sensor 10 according to the present embodiment is significantly reduced as compared to when the heating operation in the second period of time T2 is omitted. This is because a completely reverse temperature load to that in the first period of time T1 is applied to the first and second thermistors Rd1 and Rd2 to make the thermal histories of the first and second thermistors Rd1 and Rd2 coincide with each other.

The lengths of both the first and second periods of time T1 and T2 are preferably set in the range of 50 ms to 400 ms and are more preferably made to coincide with each other. That is, in the present embodiment, the first and second sensor parts S1 and S2 each have a MEMS structure, so that the time required from the start of heating by the first and second heater resistors MH1 and MH2 until the heating temperature of the first and second thermistors Rd1 and Rd2 is stabilized is about 50 ms. Further, heating beyond 400 ms, which may disadvantageously increase power consumption, is not required. Making the lengths of both the first and second periods of time T1 and T2 allows the thermal histories of the first and second thermistors Rd1 and Rd2 to completely coincide with each other.

Figure 7:
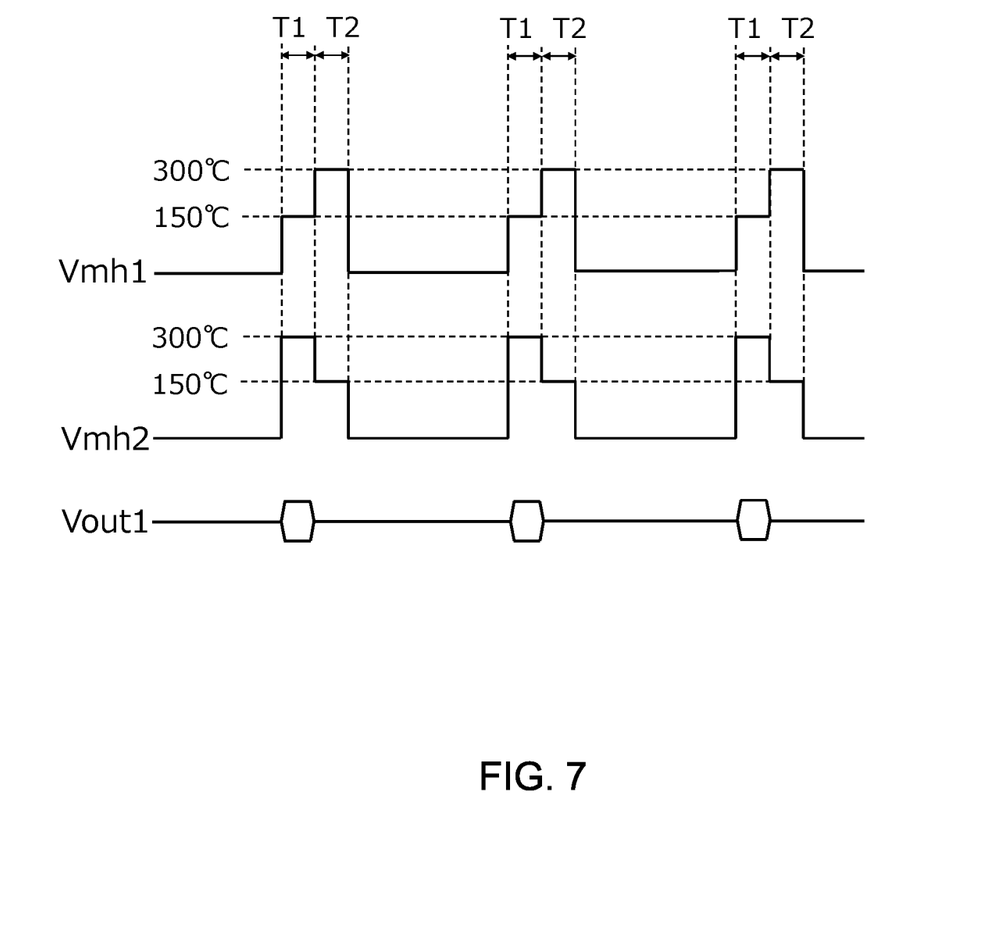
FIG. 7 is a timing chart illustrating the waveforms of the control voltages Vmh1 and Vmh2 according to a first modification.
Figure 8:
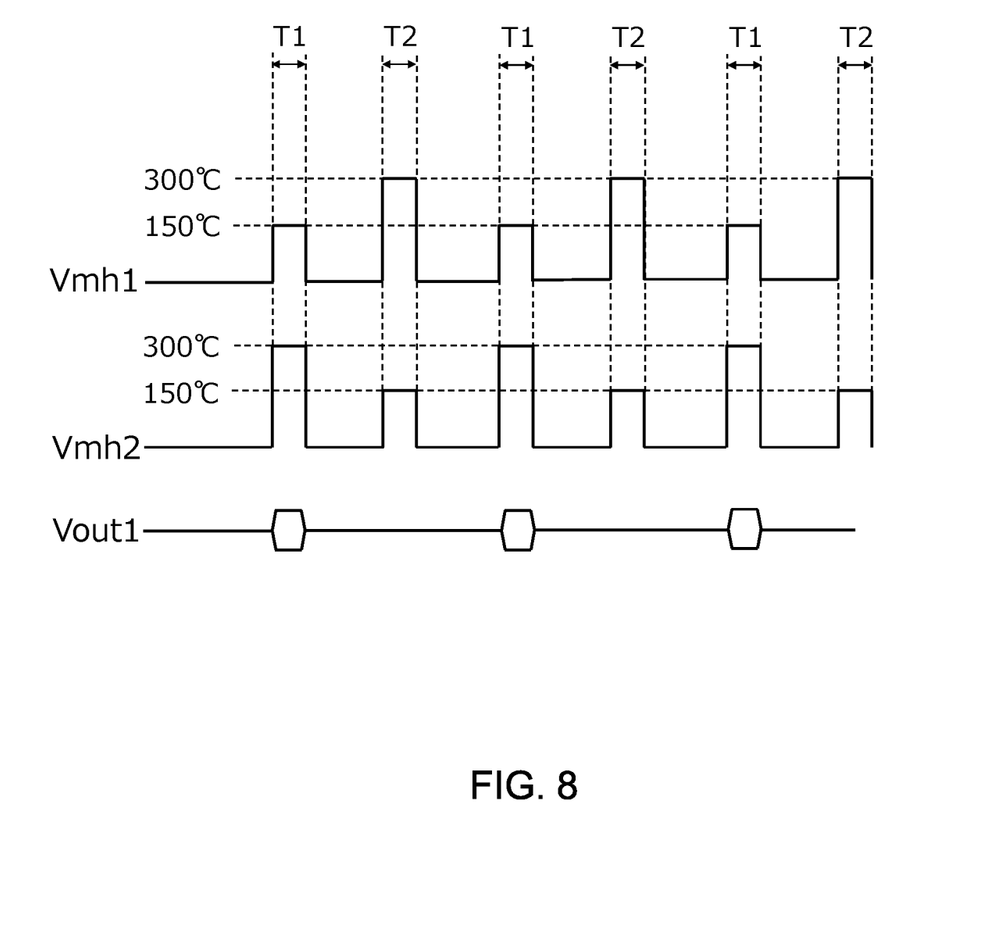
FIG. 8 is a timing chart illustrating the waveforms of the control voltages Vmh1 and Vmh2 according to a second modification.

The timing at which the second period of time T2 is inserted is not limited unless the second period of time T2 does not overlap the first period of time T1. Thus, as illustrated in FIG. 7, the second period of time T2 may be set immediately after the first period of time T1 so that they are continuous. Alternatively, as illustrated in FIG. 8, the second period of time T2 may be inserted at a timing just corresponding to the midpoint between a given first period of time T1 and its subsequent first period of time T1. However, setting the second period of time T2 immediately before the first period of time T1, which may affect actual measurement due to residual heat in the second period of time T2, should preferably be avoided.

Figure 9:
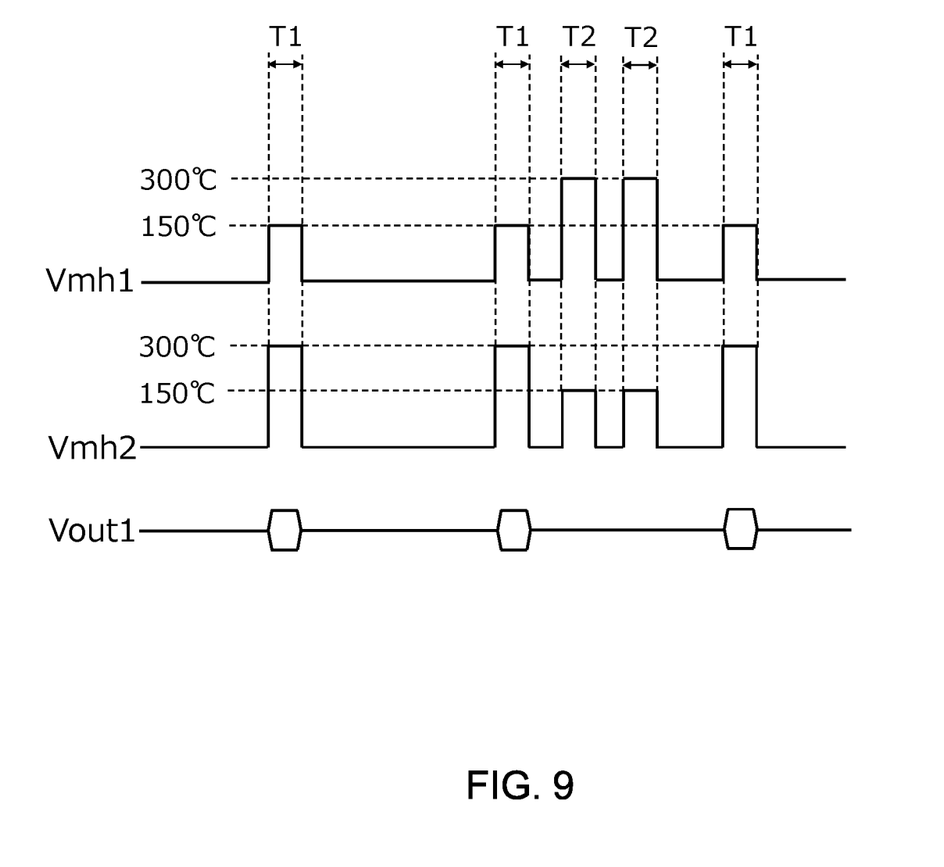
FIG. 9 is a timing chart illustrating the waveforms of the control voltages Vmh1 and Vmh2 according to a third modification.

Further, the first and second periods of time T1 and T2 need not be alternately repeated. For example, as illustrated in FIG. 9, the second period of time T2 may be inserted two times after two times of the first period of time T1.

It is apparent that the present invention is not limited to the above embodiments, but may be modified and changed without departing from the scope and spirit of the invention.

For example, although the above description has been made with the example in which the measurement target gas is $CO_2$ gas, the present invention is not limited to this. Further, the sensor part to be employed in the present invention may not necessarily be the heat conduction type sensor but may be a sensor of other types, such as a contact combustion type.

In the present embodiment, the heating temperature of the first thermistor Rd1 in the first period of time T1 and the heating temperature of the second thermistor Rd2 in the second period of time T2 are equal (150° C.), and the heating temperature of the second thermistor Rd2 in the first period of time T1 and the heating temperature of the first thermistor Rd1 in the second period of time T2 are equal (300° C.); however, this is not essential in the present invention. Further, the number of times of occurrence of the first period of time T1 per unit time and the number of times of occurrence of the second period of time T2 per unit time may not necessarily completely coincide with each other.

REFERENCE SIGNS LIST 20 control circuit
21-23 differential amplifier
24 AD converter
25 DA converter
26 signal processing part
31, 41 substrate
31a, 41a cavity
32, 33, 42, 43 insulating film
34, 44 heater protective film
35, 45 thermistor electrode
36, 46 thermistor protective film
37a-37d, 47a-47d electrode pad
51 ceramic package
52 lid
53 vent hole
54 package electrode
55 bonding wire
56 external terminal
MH1 first heater resistor
MH2 second heater resistor
R1-R3 resistor
Rd1 first thermistor (detection element)
Rd2 second thermistor (reference element)
S sensor part
S1 first sensor part
S2 second sensor part
T1 first period of time
T2 second period of time

What is claimed is:

1. A gas sensor comprising:
    a detection element whose resistance value changes in accordance with a concentration of a gas to be detected;
    a reference element connected in series to the detection element;
    a first heater for heating the detection element;
    a second heater for heating the reference element; and
    a control circuit configured to:
        heat both the first heater and the second heater such that the reference element has a higher temperature than the detection element in a first period of time; and
        heat both the first heater and the second heater such that the detection element has a higher temperature than the reference element in a second period of time.

2. The gas sensor as claimed in claim 1, wherein the control circuit calculates the concentration of the gas to be detected based on a potential appearing at a connection point between the detection element and the reference element in one of the first and second periods of time.

3. The gas sensor as claimed in claim 1, wherein the control circuit heats the first and second heaters such that the detection element and the reference element have a first temperature and a second temperature, respectively, in the first period of time and that the reference element and the detection element have the first temperature and the second temperature, respectively, in the second period of time.

4. The gas sensor as claimed in claim 1, wherein lengths of the first and second periods of time are equal to each other.

5. The gas sensor as claimed in claim 1,
    wherein the gas to be detected is $CO_2$ gas,
    wherein the heating temperature of the detection element in the first period of time is in a range of 100° C. to 200° C., and
    wherein the heating temperature of the reference element in the first period of time is in a range of 100° C. to 200° C.

6. The gas sensor as claimed in claim 1,
    wherein the detection element and reference element have a MEMS structure, and wherein a length of the first period of time is in a range of 50 ms to 400 ms.

7. The gas sensor as claimed in claim 1, wherein a ratio of a resistance value of the detection element and a resistance value of the reference element is in a range of 0.5 to 2.0.

8. The gas sensor as claimed in claim 1, wherein the detection element and reference element are formed on mutually different chips.

9. The gas sensor as claimed in claim 1,
wherein the control circuit is configured to stop heating the first and second heaters in a third period of time, and
wherein temperature of the detection element and the reference element in the first and second periods of time is higher than temperature of the detection element and the reference element in the third period of time.

10. A gas sensor comprising:
first and second thermistors connected to each other in series;
first and second heaters configured to heat the first and second thermistors, respectively; and
a control circuit configured to:
heat both the first heater and the second heater so that the first and second thermistors have first and second temperature, respectively, at a same time in a first period of time, the first temperature is different from the second temperature; and
heat both the first heater and the second heater so that the first and second thermistors have the second and first temperature, respectively, at a same time in a second period of time.

11. The gas sensor as claimed in claim 10, wherein the first and second periods of time are alternately repeated.

12. The gas sensor as claimed in claim 10,
wherein the control circuit is configured to stop heating the first and second heaters in a third period of time, and
wherein the first and second temperature is higher than temperature of the first and second thermistors in the third period of time.

13. The gas sensor as claimed in claim 10, wherein the control circuit is configured to calculate a concentration of a gas based on a potential appearing at a connection point between the first and second thermistors.

* * * * *